US007012151B1

(12) United States Patent
Schneider et al.

(10) Patent No.: US 7,012,151 B1
(45) Date of Patent: Mar. 14, 2006

(54) METHOD FOR NITRATING ANILINE DERIVATIVES

(75) Inventors: Heinrich Schneider, deceased, late of Ingelheim (DE); by Margarete Schneider, legal representative, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/958,366

(22) PCT Filed: Apr. 12, 2000

(86) PCT No.: PCT/EP00/03247

§ 371 (c)(1),
(2), (4) Date: Sep. 29, 2003

(87) PCT Pub. No.: WO00/63158

PCT Pub. Date: Oct. 26, 2000

(30) Foreign Application Priority Data

Apr. 17, 1999 (DE) .......................... 199 17 524

(51) Int. Cl.
*C07C 205/00* (2006.01)

(52) U.S. Cl. ............................ 560/20; 560/8; 562/433; 562/434

(58) Field of Classification Search ................... 560/20, 560/8; 562/433, 434
See application file for complete search history.

(56) References Cited

U.S. PATENT DOCUMENTS 4,882,342 A   11/1989  von der Saal et al.

OTHER PUBLICATIONS

Ries et al, Journal of Medicinal Chemistry, 1993, vol. 36, pp. 4040–4051.*
Monge, A. et al; "Hypoxia–Selective Agents Derived from Quinoxaline 1,4-Dl-N-oxides"; J. Med. Chem. 1995, 38, 1786–1792.
Kubo, K. et al; "Nonpeptide Angiotensin II Receptor Antagonists. Synthesis and Biological Activity of Benzimidazoles"; J. Med. Chem. 1993, 36, 1772–1784.
Ries, U. J. et al; "6–Substituted Benzimidazoles as New Nonpeptide Angiotensin II Receptor Antagonists: Synthesis, Biological Activity, and Structure—Activity Relationships": J. Med. Chem. 1993. 36. 4040–4051.

* cited by examiner

*Primary Examiner*—Rita Desai
*Assistant Examiner*—Hector M. Reyes
(74) *Attorney, Agent, or Firm*—Robert P. Raymond; Alan R. Stempel; Mary-Ellen M. Devlin

(57) ABSTRACT

The present invention relates to a process for the highly regioselective aromatic nitration of alkyl 4-alkanoylamino-3-alkyl-benzoates in the 5-position in a mixture containing nitric acid and the use of the resulting products for preparing, in particular, pharmaceutically active benzimidazole derivatives.

7 Claims, No Drawings

METHOD FOR NITRATING ANILINE DERIVATIVES

RELATED APPLICATIONS

This application is derived from International Application PCT/EP00/03247, filed Apr. 12, 2000, pursuant to 35 U.S.C. §371.

The present invention relates to a process for high regioselective aromatic nitration of alkyl 4-alkanoylamino-3-alkyl-benzoates in the 5-position in a mixture containing nitric acid, and the use of the resulting products for preparing benzimidazole derivatives having a pharmaceutical activity, in particular.

BACKGROUND OF THE INVENTION

The mononitration of amino-substituted aromatic compounds is of industrial importance since it provides a method of producing nitroanilines which are, inter alia, important intermediate compounds in the synthesis of dyes, antioxidants and especially pharmaceuticals. The mononitration of aniline derivatives in the ortho-position is of particular importance since the resulting 1,2-nitroanilines can be further reacted to form aromatic heterocycles with two heteronitrogen atoms, such as benzimidazoles.

Unfortunately, however, nitration of aromatic compounds on an industrial scale presents various problems.

Thus, the desired products are not usually obtainable in isomerically pure form since the isomeric equilibrium can only be influenced by the reaction conditions to a limited extent, as is well known, during the mononitration of differently substituted aromatic compounds (cf. for example the industrial mononitration of toluene: K. Weissermehl, H.-J. Arpe, Industrielle organische Chemie, 3rd Edition page 400–401). The separation of the desired regioisomer frequently proves very difficult. However, for industrial synthesis of pharmaceuticals, it is essential to be able to obtain extremely pure products in the individual reaction steps.

Another problem with nitration on an industrial scale is the safety risk, which is sometimes considerable. Thus, on the one hand, the reaction solutions required for the nitration of aromatic compounds are usually highly explosive, particularly when concentrated nitric acid is used as the nitrating agent. The reaction process is particularly dangerous when the accumulation of reaction compounds is very great. In such cases the individual reactants do not react immediately when combined but after a certain time delay. As a result, continuous and hence controlled conduct of the reaction is made difficult and the risk of a spontaneous explosive reaction increases. Another safety risk which is hard to calculate is presented by the products which are produced by the reaction. Di- and tri-nitrated by-products are particularly risky in this respect. The latter may in some cases be produced spontaneously in industrial-scale nitration processes, so that they are outside the control of those responsible for the process.

DESCRIPTION OF THE INVENTION

It is therefore the aim of the present invention to provide a large scale industrial process for the mononitration of alkyl 4-alkanoylamino-3-alkyl-5-nitrobenzoates, which overcomes the disadvantages known from the prior art.

A particular objective of the invention is to provide an industrial-scale highly regioselective process for aromatic nitration of alkyl 4-alkanoylamino-3-alkyl-benzoates in the 6-position in which the formation of isomers and possibly di- and/or trinitrated alkyl 4-alkanoylamino-3-alkyl-benzoates is minimised or totally suppressed.

A further objective of the present invention is to provide a process for use on an industrial scale for the aromatic nitration of alkyl 4-alkanoylamino-3-alkyl-benzoates which allows easy isolation of the alkyl 4-alkanoylamino-3-alkyl-5-nitrobenzoates formed.

Finally, the invention also sets out to produce alkyl 4-alkanoylamino-3-alkyl-5-nitrobenzoates on an industrial scale, which can be further reacted to produce pharmacologically active benzimidazoles.

DETAILED DESCRIPTION OF THE INVENTION

Surprisingly, it has been found that alkyl 4-alkanoylamino-3-alkyl-5-nitrobenzoates of general Formula I,

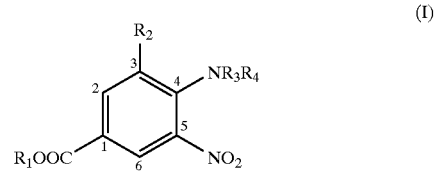

(I)

wherein
$R_1$ denotes H or $C_{1-6}$-alkyl,
$R_2$ denotes H or $C_{1-6}$-alkyl;
$R_3$ denotes H;
$R_4$ denotes H or $C_{1-5}$-alkyl-carbonyl
or $R_3$ and $R_4$ together denote succinyl, glutaryl or adipinyl, can be produced, totally unexpectedly, in substantially isomerically pure form, from alkyl 4-alkanoylamino-3-alkyl-benzoates according to general Formula II

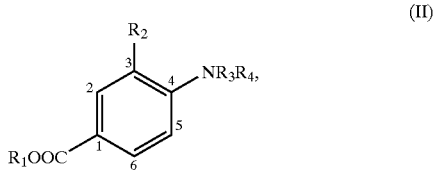

(II)

wherein $R_1$, $R_2$, $R_3$ and $R_4$ have the meanings given in Formula I, by dissolving the alkyl 4-alkanoylamino-3-alkyl-benzoate of Formula II, in a first step, in a mixture of sulphuric acid, nitric acid and water without reacting them and, in a second step, by adding nitric acid as the nitration agent, reacting to form substantially isomerically pure alkyl 4-alkanoylamino-3-alkyl-5-nitrobenzoate of general Formula I.

Accordingly, the process according to the invention solves the problem by dissolving the educt, alkyl 4-alkanoylamino-3-alkyl-benzoate according to Formula II, in a first step, in a mixture of water, sulphuric acid and nitric acid in such a way that it does not react or substantially does not react. In a second step the highly regioselective reaction to obtain alkyl 4-alkanoylamino-3-alkyl-5-nitrobenzoate of general Formula I is carried out by the addition of a nitration agent.

A preferred process relates to the preparation of alkyl 4-alkanoylamino-3-alkyl-5-nitrobenzoates of general Formula I, wherein the groups are defined as follows:

$R_1$ denotes H, methyl, ethyl, propyl, isopropyl, butyl, isobutyl, pentyl, hexyl;

$R_2$ denotes H, methyl, ethyl, propyl, isopropyl, butyl, isobutyl, pentyl, hexyl;

$R_3$ denotes H;

$R_4$ denotes H, acetyl, propionyl, butyryl, valeryl, capryl, or $R_3$ and $R_4$ together may form a succinyl-, glutaryl- or adipinyl group. Particularly preferred are alkyl 4-alkanoylamino-3-alkyl-5-nitrobenzoates of general Formula I wherein $R_1$ denotes methyl; $R_2$ denotes methyl; $R_3$ denotes butyryl and $R_4$ denotes H.

Accordingly, alkyl 4-alkanoylamino-3-alkyl-benzoates of general Formula II are preferably used wherein groups $R_1$, $R_2$, $R_3$ and $R_4$ are as hereinbefore defined. The acids used are preferably put in in concentrated form; in particular, sulphuric acid is used as 96% by weight sulphuric acid and nitric acid as approximately 98–100% by weight nitric acid In a preferred embodiment the components nitric acid, sulphuric acid and water for the mixture for dissolving the educt in the first step of the process are used in a molar ratio of 1.5–2.5 mol of nitric acid to 1.5–2.5 mol of sulphuric acid to 2–6 mol of water per mol of educt to be reacted. A preferred molar ratio of the components is 1.8–2.2 mol of nitric acid to 1.8–2.2 mol of sulphuric acid to 2.5–4.0 mol of water per mol of educt to be reacted. A particularly preferred molar ratio of the components is 2 mol of nitric acid to 2 mol of sulphuric acid to 3 mol of water per mol of educt to be reacted.

In the first step of the process the educt is added to the solvent continuously or batchwise at less than 10° C., preferably below 0° C., and dissolved therein. The preferred temperature is between −20° C. and 10° C., most preferably between −10° C. and −5° C.

The educt thus dissolved in the mixture described above is nitrated in a second step of the process.

The nitration agent used may be any of the reagents known from the prior art, such as $HNO_3$, $N_2O_5$, methylnitrate and $BF_3$, $NaNO_2$, $N_2O_4$, $NO_2BF_4$, $NO_2PF_6$, $NO_2CF_3SO_3$, organic nitro compounds and others. The preferred nitration agent is nitric acid, particularly 98–100% by weight nitric acid. It should be pointed out here that the quantity and concentration of nitric acid used in the first step for the mixture in order to dissolve the educt is not sufficient to nitrate the educt, which means that the quantity of nitric acid required for the nitration has to be slowly adjusted in this second step by the addition of further nitric acid. The quantity of nitric acid needed for the nitration varies within a tolerance range of 6 to 10 mol per mol of educt to be nitrated, preferably 7–9 mol per mol of educt, most preferably about 8 mol per mol of educt. It is added continuously or batchwise over a period of more than 2 hours. Preferred addition times range from 2 to 6 hours, most preferably 3 to 4 hours. During the addition the reaction temperature is maintained at −20° C. to +10° C., preferably at −5° C. to +5° C.

After the reaction has ended the mixture is added to water. To minimise or completely avoid consequent reactions of the product with water, care must be taken to ensure that the aqueous mixture does not exceed a temperature of +50° C.; the upper temperature range of the mixture is preferably between 30° C. and +40° C.

Substantially isomerically pure alkyl 4-alkanoylamino-3-alkyl-5-nitrobenzoate of general Formula I is obtained as the product of the process according to the invention. The term isomerically pure or substantially isomerically pure denotes, in the present context, alkyl 4-alkanoylamino-3-alkyl-5-nitrobenzoates of general Formula I which are wholly or largely free from alkyl 4-alkanoylamino3-alkyl-6-nitrobenzoates and/or alkyl 4-alkanoylamino-3-alkyl-2-nitrobenzoates, the substituents $R_1$, $R_2$, $R_3$, and $R_4$ being identical in the latter three compounds. The total content of 2- and 6-nitroisomer is less than 2 mol %, based on the main product.

Another advantage of the process described is its comparatively high safety. This is also reflected in the fact that, when the nitric acid is metered over a period of 3 h in the second step, the accumulation of reaction compounds is about 5–10%. This means that the nitration of the educt takes place so fast that, on average, not more than 5–10% of the reactants which are to be reacted are present in unreacted form during the dropwise addition of the nitric acid. This has the advantage that even if the coolant or other energies should fail the reaction mass can only heat up to a limited extent which is still not within the range of a self-accelerating decomposition.

On the basis of what has already been said, a preferred embodiment of the invention relates to a nitration process for the highly regioselective preparation of alkyl 4-alkanoylamino-3-alkyl-5-nitrobenzoates of general Formula I wherein $R_1$ denotes H or $C_{1-6}$-alkyl; $R_2$ denotes H or $C_{1-6}$-alkyl; $R_3$ denotes H; $R_4$ denotes H or $C_{1-5}$-alkyl-carbonyl or $R_3$ and $R_4$ together may denote succinyl, glutaryl or adipinyl, which is characterised in that alkyl 4-akanoylamino-3-alkyl-benzoate of Formula II, wherein $R_1$, $R_2$, $R_3$ and $R_4$ are as hereinbefore defined is dissolved, in a first step, in a mixture of water, sulphuric acid and nitric acid and in a second step the mixture is combined with nitric acid.

A preferred nitration process of this kind is one wherein the ratio of the components of the solvent mixture for the first step is 1.5–2.5 mol of sulphuric acid to 1.5–2.5 mol of nitric acid per mol of alkyl 4-alkanoylamino-3-alkyl-benzoate of Formula II to 2–6 mol of water.

Also preferred is a nitration process of this kind wherein the quantity of nitric acid in the second step is 6–10 mol of nitric acid per mol of alkyl 4-alkanoylamino-3-alkyl-benzoate of Formula II.

A preferred nitration process is one which is characterised in that the components of the solvent mixture of the first step are in a molar ratio of 1.8–2.2 mol of nitric acid to 1.8–2.2 mol of sulphuric acid to 2.5–4.0 mol of water per mol of alkyl 4-alkanoylamino-3-alkyl-benzoate of Formula II and in the second step 7–9 mol of nitric acid are added per mol of alkyl 4-alkanoylamino-3-alkyl-benzoate of Formula II.

Particularly preferred is a nitration process of this kind wherein the ratio of the components of the solvent mixture of the first step is 2 mol of nitric acid to 2 mol of sulphuric acid to 3 mol of water per mol of alkyl 4-alkanoylamino-3-alkyl-benzoate of Formula II and in the second step 8 mol of nitric acid are added per mol of alkyl 4-alkanoylamino-3-alkyl-benzoate of Formula II.

In an equally preferred embodiment of a nitration process of this kind the alkyl 4-alkanoylamino-3-alkyl-benzoate of Formula II is preferably added to the solvent mixture in the first step at −20 to +10° C.

In another preferred embodiment of a nitration process of this kind the nitric acid is added in the second step at a temperature of between −10 and +10° C., preferably at −5 to +5° C.

In all the embodiments, nitration processes are particularly preferred wherein the groups $R_1$, $R_2$, $R_3$ and $R_4$ are defined as follows:

$R_1$ denotes H, methyl, ethyl, propyl, isopropyl, butyl, isobutyl, pentyl, hexyl; $R_2$ denotes H, methyl, ethyl, propyl, isopropyl, butyl, isobutyl, pentyl, hexyl; R$_3$ denotes H; R$_4$ denotes H, acetyl, propionyl, butyryl, valeryl, capryl or R$_3$ and R$_4$ together form a succinyl-, glutaryl- or adipinyl-group. Particularly preferred are those compounds wherein R$_1$ is methyl; R$_2$ is methyl; R$_3$ is butyryl and R$_4$ is H.

The alkyl 4-alkanoylamino-3-alkyl-5-nitrobenzoates of general Formula I which can be prepared by the method described above are important components for the synthesis of benzimidazoles, particularly those of Formula 3

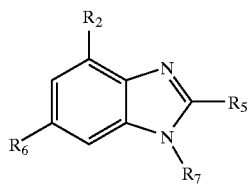

(III)

having the groups R$_2$=methyl; R$_5$=propyl; R$_6$=N-methylbenzimidazol-2-yl- or COOR$_1$, where R$_1$, is defined in Formula 1 and R$_7$ is H, to which they can be reacted by simple subsequent reactions.

The benzimidazoles and salts thereof which are thus obtained or further derivatised are of great value owing to their pharmacological versatility. They are used, for example, for treating hypertension and cardiac insufficiency, for treating ischaemic peripheral circulatory disorders, myocardiac ischaemia (Angina), for preventing the progression of cardiac insufficiency after myocardial infarct, for treating diabetic neuropathy, glaucoma, gastrointestinal and bladder diseases and they may also have an anthelmintic activity.

The alkyl 4-alkanoylamino-3-alkyl-5-nitrobenzoates of general Formula I may be reacted, for example, by the process described in the Journal of Medicinal Chemistry 1993, Vol. 36, No. 25 pages 4040–4051 to produce benzimidazoles and derivatives thereof. In particular, the compound of general Formula I wherein R$_1$ is methyl; R$_2$ is methyl; R$_3$ is H and R$_4$ is butyryl may be prepared using reaction scheme V described on page 4050. Other possible reactions can be found for example in European Patent EP 0 502 314 B1. By way of example, reference is made particularly to the reaction of nitrated methyl 3-methyl-4-n-butanoyl-aminobenzoate described on page 11, line 23 ff of EP 0 502 314 B1. The invention therefore also relates to benzimidazoles, particularly one of Formula III, prepared by a process which comprises one of the steps described above for nitrating alkyl 4-alkanoylamino-3-alkyl-benzoates of Formula II having the groups R$_1$, R$_2$, R$_3$ and R$_4$ as defined above. In particular, it relates to one such process for preparing 2-propyl-4-methyl-6-methoxycarbonylbenzimidazole wherein methyl 4-butyrylamino-3-methyl-benzoate is nitrated by a process as described above, then the nitro group is reduced to form the primary amine and finally the carbonyl function of the butyryl group is condensed with the primary aminofunction. In a subsequent reaction the methylester of 2-propyl-4-methyl-6-methoxycarbonylbenzimidazole may be saponified and reacted with N-methyl-o-phenylenediamine to form 2-propyl-4-methyl-6-(N-methylbenzimidazol-2-yl)-benzimidazole.

EXAMPLES 27.5 l of water and 122.5 kg of 96% sulphuric acid are placed in a 500 l enamel stirring apparatus and cooled to −10° C. First, 76.4 kg of 99% nitric acid are metered in at about −10 to 0° C. and then within 1–2 h 141 kg of methyl 4-butyrylamino-3-methylbenzoate are added through the manhole at −10 to −5° C. Then a further 305.5 kg of 99% nitric acid are metered in within 3–4 hours at −5 to +5° C. The mixture is stirred thoroughly for another 30–60 minutes while the temperature is allowed to rise to +5 to 10° C. This mixture is then added at 35–40° C., with stirring, to a 1200 l enamel stirring apparatus charged with 564 l of water. It is rinsed with 141 l of water and cooled to 15–20° C. The product precipitated is separated by centrifuging, washed with water and dried.

Yield: 153 kg of methyl 4-butyrylamino-3-methyl-5-nitrobenzoate, practically free from isomers (91% of theory).

Comparative Reactions with Processes Known from the Prior Art

Comparison Example A 45 l of water and 130 kg of 96% sulphuric acid are placed in a 500 l enamel stirring apparatus. At a maximum 20° C. 209.5 kg of 99% nitric acid are metered in, cooled to about −10° C. and then 35.3 kg of methyl 4-butyrylamino-3-methylbenzoate are added through the manhole at −10 to −5° C. The mixture is stirred thoroughly for a further 15 minutes, the temperature is allowed to rise to 0° C. and stirred thoroughly for another 1 h. The mixture is then added to a 1200 l enamel stirring apparatus charged with 400 kg of ice and 500 l of water, at max. +10° C. over 1.5–2 h and then stirred for a further 30 minutes approximately. The product precipitated is separated by centrifuging, washed with water and dried.

Yield: 37 kg of methyl 4-butyrylamino-3-methyl-5-nitrobenzoate (88% of theory), the product contains about 8–10% of methyl 4-butyrylamino-3-methyl-6-nitrobenzoate and about 1–2% of methyl 4-butyrylamino-3-methyl-2-nitrobenzoate.

Comparison Example B 70.5 g of 96% sulphuric acid are placed in a 500 ml flask and 23.5 g of methyl 4-butyrylamino-3-methylbenzoate are added at max. 20° C. Then 36.2 g of mixed acid (about 65% sulphuric acid and 35% nitric acid) are metered in at −10 to 0° C. over about 60 minutes. The resulting mixture is stirred for a further 60 minutes and then poured onto a mixture of 250 g of ice and 250 ml of water. The product precipitated is suction filtered, washed with water and dried.

Yield: 24.9 g of methyl 4-butyrylamino-3-methyl-5-nitrobenzoate (89% of theory), the product contains about 8–10% of methyl 4-butyrylamino-3-methyl-6-nitrobenzoate and about 1–2% of methyl 4-butyrylamino-3-methyl-2-nitrobenzoate.

What is claimed is:

1. A process for preparing an alkyl 4-alkanoylamino-3-alkyl-5-nitrobenzoate of the formula I

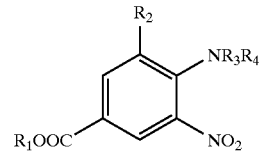

(I)

wherein
 R$_1$ is H or C$_{1-6}$-alkyl;
 R$_2$ is H or C$_{1-6}$-alkyl;

$R_3$ is H; and
$R_4$ is H or $C_{1-5}$-alkyl-carbonyl,
or $R_3$ and $R_4$ together form a succinyl, glutaryl or adipinyl group, which process comprises the following steps:
(a) dissolving an alkyl 4-alkanoylamino-3-alkyl-benzoate of the formula II

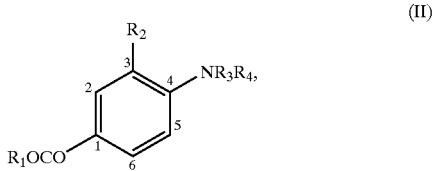

wherein $R_1$, $R_2$, $R_3$ and $R_4$ are as hereinbefore defined, at a temperature that is less than 10° C., in a solvent mixture comprising 1.5–2.5 mol of sulphuric acid, 1.5–2.5 mol of nitric acid and 2–6 mol of water per mol of the alkyl 4-alkanoylamino-3-alkyl-benzoate of formula II and,
(b) at a temperature between −20 and +10° C., nitrating the compound of formula II by adding to the mixture produced by step (a) 6–10 mol of nitric acid per mol of the alkyl 4-alkanoylamino-3-alkyl-benzoate of formula II, to yield the compound of formula I.

2. The process according to claim 1, wherein the components of the solvent mixture used in step (a) are in a molar ratio of 1.8–2.2 mol of nitric acid to 1.8–2.2 mol of sulphuric acid to 2.5–4 mol of water per mol of alkyl 4-alkanoylamino-3-alkyl-benzoate of the formula II and wherein, in step (b), 7–9 mol of nitric acid are added per mol of alkyl 4-alkanoylamino-3-alkyl-benzoate of the formula II.

3. The process according to claim 1, wherein the components of the solvent mixture used in step (a) are in a molar ratio of 2 mol of nitric acid to 2 mol of sulphuric acid to 3 mol of water per mol of alkyl 4-alkanoylamino-3-alkyl-benzoate of the formula II and wherein, in step (b), 8 mol of nitric acid are added per mol of alkyl 4-alkanoylamino-3-alkyl-benzoate of the formula II.

4. The process according to claim 1, wherein step (a) is carried out at a temperature between −20 and +10° C.

5. The process according to claim 1, wherein step (b) is carried out at a temperature between −5 and +5° C.

6. The process according to claim 1, wherein:
$R_1$ is H, methyl, ethyl, propyl, isopropyl, butyl, isobutyl, pentyl, hexyl;
$R_2$ is H, methyl, ethyl, propyl, isopropyl, butyl, isobutyl, pentyl, hexyl;
$R_3$ is H; and
$R_4$ is H, acetyl, propionyl, butyryl, valeryl, capryl,
or $R_3$ and $R_4$ together form a succinyl-, glutaryl- or adipinyl-group.

7. The process according claim 1, wherein:
$R_1$ is methyl;
$R_2$ is methyl;
$R_3$ is H; and
$R_4$ is butyryl.

* * * * *